United States Patent [19]

Siuta-Mangano et al.

[11] Patent Number: 4,613,689

[45] Date of Patent: Sep. 23, 1986

[54] RACEMIZATION OF OPTICALLY ACTIVE COMPOUNDS HAVING A CHLORINE SUBSTITUTED CHIRAL CARBON ATOM

[75] Inventors: Patricia Siuta-Mangano, Mount Vernon; Samun K. Dahod, Yorktown Heights, both of N.Y.

[73] Assignee: Stauffer Chemical Company, Westport, Conn.

[21] Appl. No.: 771,091

[22] Filed: Aug. 30, 1985

[51] Int. Cl.$^4$ .............................................. C07B 55/00
[52] U.S. Cl. .................................... 562/401; 562/402; 562/490; 562/492; 562/493; 562/602
[58] Field of Search ................................ 562/401, 402

[56] References Cited

U.S. PATENT DOCUMENTS 4,245,116  1/1981  Ohno et al. ........................ 562/401

Primary Examiner—Natalie Trousof
Assistant Examiner—Vera C. Clarke
Attorney, Agent, or Firm—Paul J. Juettner

[57] ABSTRACT

Optically active compounds having a chlorine atom attached to the chiral carbon atom such as 2-chloroaliphatic acids can be racemized without by-product formation by heating an acidified solution of the compound in the presence of chloride ion at sufficient strength, and at a pH and temperature sufficient to accomplish racemization. The preferred acidifying agent and source of chloride ion is hydrochloric acid. The use of hydrochloric acid at room temperature as well as the use of either sulfuric acid or caustic soda failed to produce racemization.

14 Claims, No Drawings

RACEMIZATION OF OPTICALLY ACTIVE COMPOUNDS HAVING A CHLORINE SUBSTITUTED CHIRAL CARBON ATOM

FIELD OF THE INVENTION

The present invention relates to a process for racemizing optically active compounds having a chlorine atom attached to the chiral carbon atom such as 2-chloroaliphatic acids.

BACKGROUND OF THE INVENTION

Certain herbicides such as napropamide, chemical name: 2-(alpha-naphthoxy)-N,N-diethylpropionamide, are active only in the dextro (+) isomeric form. (Synthesis and Herbicidal Activity of N,N-Diethyl-2-(1-naphthyloxy)propionamide & Its Optical Isomers—Agricultural & Food Chemistry, Vol. 23, 5 (September/October 1975) pp. 1008–1010). It is known that the dextro isomer of napropamide can be prepared from L-methyl-2-chloropropionate. This material is not presently available at a price which can be economically utilized in the process of preparing napropamide as suggested above. Enzymes have shown stereospecificity in resolving mixtures of D,L-methyl-2-chloropropionate into L-methyl-2-chloropropionate and D-2-chloropropionic acid. In order for such a resolution method to provide an economical process it is necessary to racemize and reesterify the D-2-chloropropionic acid for resolution and use in manufacturing the desired product.

THE INVENTION

Optically active compounds having a chlorine atom attached to the chiral carbon atom(s), such as chloroaliphatic acids, can be racemized by treatment of an acidified solution of the optically active compound with chloride ion in an amount sufficient and at a pH and temperature sufficient to accomplish racemization. Preferably, the chloride ion is provided by hydrochloric acid. It has been surprisingly found that sulfuric acid or caustic soda fails to produce racemization. Racemization is not accomplished by treating optically active 2-chloroaliphatic acid with hydrochloric acid at room temperature. The racemization with chloride ion under acidic pH such as with hydrochloric acid proceeds easily and cleanly without producing yield reducing by-products.

DETAILED DESCRIPTION OF THE INVENTION

The compounds that can be racemized in accordance with the present invention are those optically active compounds having a chlorine atom attached to a chiral carbon atom. The chiral carbon atom is not contained in an aromatic or homogeneous or heterogeneous alicyclic ring. The chiral carbon atom is so located within the optically active compound that the groups attached to the chiral carbon do not prevent racemization. The preferred compounds are carboxylic acids which can have an aromatic, e.g. phenylene, or an aliphatic group, e.g. alkylidene, connecting the carboxylic acid group with the chiral carbon atom. Preferably, the compounds are carboxylic acids wherein the chiral carbon is attached to the carboxylic acid group. The chiral carbon atom has attached to it other carbon atoms or a hydrogen atom in addition to the chlorine atom wherein each is different. A particularly preferred group of compounds which can be racemized in accordance with the invention are the optically active chloroaliphatic acids which can be represented by the formula

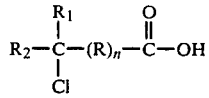

wherein R can be aliphatic or aromatic, n can be an integer of 1 or zero, $R_1$ and $R_2$ each can be hydrogen or alkyl of up to 20 carbon atoms wherein $R_1$ and $R_2$ are different. R can be an organic ring (1 or 2), e.g. phenylene, or aliphatic, e.g. alkyl of up to 20 carbons, as long as the groups do not prevent the racemization. Preferably, n is zero, $R_1$ is $C_1$–$C_4$ and more preferably $C_1$–$C_2$ and most preferably $C_1$. $R_2$ is preferably hydrogen. Illustrative of the 2-chloroaliphatic acids which can be racemized in accordance with the invention are D-2-chloropropionic acid, L-2-chloropropionic acid, D-2-chlorobutyric acid, D-2-chloropentanoic acid and the like.

The following discussion will continue in connection with the preferred optically active chloroaliphatic acid, illustrated by D-2-chloropropionic acid, though the discussion is intended to cover the other optically active compounds falling within the scope of the invention.

The racemization of the optically active chloroaliphatic acid in accordance with the invention is generally conducted in the presence of a sufficient amount of water to effect ionization of the chlorine from the source of chloride ion to the extent needed for racemization. Preferably, an aqueous solution having from about 1% to about 50% chloroaliphatic acid is used. This solution can be made up from the purified acid or, preferably, the solution results from the resolution of a racemic mixture of the acid esters. In the preferred embodiment, an aqueous solution of the chloroaliphatic acid results from the resolution of a racemic mixture of the ester with a stereospecific enzyme. For example, the lipase enzyme from the yeast *Candida cylindracea* has been known to hydrolyze the D-isomer ester of 2-chloropropionic acid to thereby resolve the so formed D-isomer acid from the L-isomer ester.

The chloride ion (chlorine in ionized form) can be obtained from any source which provides the ion under the conditions of reaction and whose cation does not affect the racemization or stability of the reactants or final product. Preferably, hydrochloric acid is used as the source of chloride ion and also the acidifying agent. Other sources of chloride ion include soluble metal chlorides which can provide chloride ion under the conditions of the racemization. For example, chlorides of metals of Groups I and II of the Periodic Table of Elements illustrated by sodium chloride, potassium chloride, lithium chloride and calcium chloride and the like can be used. The chloride ion is present in an amount sufficient to effect racemization under the reaction conditions. Preferably, the chloride ion concentration is at least about 0.1N based on the molecular weight of the acid being racemized.

The racemization of the optically active chloroaliphatic acids as well as the rate of racemization is pH dependent. The racemization proceeds upon heat treatment at pH's sufficiently low to effect racemization, e.g. racemization proceeds at pH's below about 4 although slowly. Preferably, the pH is below 2.5 for effective reactive rates. The pH is preferably adjusted by the source of the chloride ion. The preferred source of chloride ion is hydrochloric acid. The concentration of hydrochloric acid in the aqueous solution is that amount which is sufficient to effect racemization when heated. The hydrochloric acid is preferably used in an amount sufficient to provide an acid concentration ranging from about 0.1 to about 6N and preferably from about 1 to about 2.5N in the aqueous solution of 2-chloroaliphatic acid to be racemized. Hydrochloric acid such as in normalities of from about 1 to about 12N or hydrogen chloride gas can be added to an aqueous solution of 2-chloroaliphatic acid to provide the desired concentration of hydrochloric acid. Any acid which is sufficiently acidic and not adverse to the reaction can be used to adjust pH, particularly when the source of chloride ion is from a source other than hydrochloric acid. Organic acids such as trichloroacetic acid (which does not contribute chloride ion to the solution) and preferably mineral acids such as sulfuric acid can be used to acidify the solution. Mineral acids are preferred as they are stronger acids than the organic acids and more economical.

The temperature utilized in the racemization reaction is that amount which is sufficient to racemize the optically active acid preferably to an enantiomeric excess of less than about 50% and more preferably less than about 30% "Enantiomeric excess" is defined as the difference between the predominant optical isomer and subdominant optical isomer. At a ratio of 75:25, the enantiomeric excess is 50%; at 65:35 the excess is 30% and at a ratio of 50:50, the excess is zero. The temperature of treatment preferably ranges from about 50° C. up to and including the reflux temperature of the acid containing the optically active acid medium. More preferably, reflux temperature is used for the racemization reaction.

The racemization is conducted for a time sufficient to allow the desired racemization in the presence of the chloride ion such as from the hydrochloric acid and at the temperature outlined hereinbefore.

The racemization can be conducted in any type of appropriate equipment. Since the process can be used as an adjunct to a process for preparing an L-isomer ester, the racemization can be conducted in equipment and under conditions which can allow subsequent reesterification of the D,L-isomer acid. It has been found that racemization and reesterification cannot be accomplished simultaneously.

The process of the present invention allows for the easy racemization or partial racemization of D-2-chloropropionic acid. The process of the present invention has the further benefit that the reaction produces no by-products. This factor facilitates the use of the resulting racemate in further resolution processes after reesterification. By "no by-product formation" is meant that at least 90% of the original optically active acid is recovered after racemization.

The invention will be more fully illustrated in the examples which follow.

EXAMPLE 1

Three milliliters of 10% D-2-chloropropionic acid solution obtained in an aqueous phase as by-product from the resolution of D,L-methyl-2-chloropropionate by enzymatic hydrolysis having an optical rotation of +4.784° heated at reflux for one hour with 97 milliliters of 6N hydrochloric acid. After cooling, the product was extracted with anhydrous ether. A concentrated oil having an optical rotation of +0.050° obtained indicating complete racemization.

EXAMPLES 2-5

Two milliliters of D-2-chloropropionic acid having an optical rotation of +3.777° (2 and 3) or +4.584° (4 and 5) were refluxed with 65 milliliters of hydrochloric acid at concentrations of 1N, 2N, 1N and 2.5N for 2, 2, 4 and 2 hours respectively. After cooling and extraction with equal volumes of ether, the following results were obtained from the concentrated product:

TABLE I

| Example | Control | Example | % D-isomer | % L-isomer |
|---------|---------|---------|-----------|-----------|
| 2 | +3.777° | +1.437° | 55 | 45 |
| 3 | +3.777° | +0.351° | 51 | 49 |
| 4 | +4.584° | +0.392° | 51 | 49 |
| 5 | +4.584° | +0.170° | 50.6 | 49.4 |

Racemization was obtained at various hydrochloric acid concentrations when heated for various periods of time.

EXAMPLE 6

100 milliliters of a solution containing 10% D-2-chloropropionic acid was refluxed for 4.75 hours with 9 milliliters of 1N hydrochloric acid. Upon cooling and extraction with ether, the concentrated product, after storage for a weekend, showed an optical rotation of +0.044° was compared to +13.08° for the pure acid. Substantially complete racemization occurred (50.2% D-isomer, 49.8% L-isomer) with substantially 100% recovery of 2-chloropropionic acid.

EXAMPLE 7

(Control)

Two milliliters of D-2-chloropropionic acid having an optical rotation of 3.777° was mixed with 65 milliliters of 1N or 3N hydrochloric acid at room temperature with stirring for 4 hours. After extracting with 70 milliliters of ether the optical rotations were recorded:
Control +3.777°
1N HCl +3.333°
3N HCl +3.548°
These results show that room temperature treatment of D-2-chloropropionic acid with hydrochloric acid did not affect racemization.

EXAMPLE 8

(Control)

D-2-chloropropionic acid whose pH was adjusted to about 7 with sodium hydroxide was dried, dissolved in 1N hydrochloric acid and adjusted to pH 2 with 6N hydrochloric acid. The optical rotation of a concentrated sample extracted with ether from the hydrochloric acid solution was observed as +4.698°.

Four milliliters of the D-2-chloropropionic acid was heated for 2 hours at 50°–55° C. with stirring with 6 milliliters of water and 1 milliliter of concentrated (96% by weight) sulfuric acid. After extraction with twice the volume of ether, the observed optical rotation was +4.123°. Sulfuric acid did not affect racemization.

EXAMPLE 9

(Control)

Forty-five milliliters of an aqueous solution containing about 13% D-2-chloropropionic acid was admixed with concentrated sulfuric acid to a level of 10% weight to volume of the reaction mixture. Some solids precipitated. The mixture was stirred and heated to reflux for over 1.5 hours. After cooling, neutralizing with sodium hydroxide and drying, the dried product was partially redissolved in hydrochloric acid at pH 1.5. The solids were filtered off and the product extracted with ether. No racemization was found in the concentrated oil.

EXAMPLE 10

(Control)

The pH of a 40 milliliters of an aqueous solution containing about 13% D-2-chloropropionic acid was adjusted to 10.7 with 50% sodium hydroxide. A precipitate was formed which did not dissolve on heating. The mixture was refluxed for 1.5 hours, cooled and neutralized to pH 7 with 6N hydrochloric acid. After drying, the product was redissolved in 1N HCl at pH 1.5-2.0. The solids were filtered and the product extracted with ether. No racemization was observed when the product was checked for optical rotation.

EXAMPLE 11-13

(Control) (Under Basic Conditions)

5.5 milliliter samples of the aqueous phase resulting from the enzymatic resolution of D,L-methyl-2-chloropropionate and containing 20% D-2-chloropropionic acid were treated with 1N sodium hydroxide sufficient to elevate the pH to the desired level. One milliliter of 0.5 molar sodium borate was added to Examples 11 and 12 to maintain the pH and the mixtures heated for 2 hours at 50°-55° C. After storage overnight the products were stirred for 2 more hours at 55° C. Examples 11-12 had a pH of about 9.5 while Example 13 had a pH of about 4.5. All pH's were adjusted to the pH of about 2 with hydrochloric acid. After the extraction the optical rotation of Examples 11 and 12 were observed to be +0.477° and +0.409° respectively. The optical rotation of the pure acid is +0.470°. No racemization was accomplished. What is claimed is:

1. A process for racemizing an optically active organic acid of the formula:

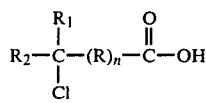

wherein R can be aliphatic or aromatic, $R_1$ and $R_2$ can each be hydrogen or alkyl of up to 20 carbon atoms wherein $R_1$ and $R_2$ are different and n is an integer of zero or 1 comprising heating an acidified solution of said optically active organic acid in the presence of a chloride ion in an amount sufficient and at a pH and temperature sufficient to racemize said acid.

2. The process as recited in claim 1 wherein n is zero.

3. The process as recited in claim 1 wherein $R_1$ is hydrogen.

4. The process as recited in claim 1 wherein said acid is a chloroaliphatic acid.

5. The process as recited in claim 4 wherein said chloroaliphatic acid is 2-chloropropionic acid.

6. The process as recited in claim 5 wherein said chloroaliphatic acid is D-2-chloropropionic acid.

7. The process as recited in claim 1 wherein the source of said chloride ion is hydrochloric acid.

8. The process as recited in claim 1 wherein the source of said chloride ion is a metal chloride.

9. The process as recited in claim 7 wherein said hydrochloric acid is used in an amount sufficient to provide a concentration of from about 0.1N to about 6N in an aqueous solution of said optically active organic acid.

10. The process as recited in claim 1 wherein said heating is conducted at a temperature ranging from about 50° C. to reflux.

11. The process as recited in claim 10 wherein said heating is at reflux temperature.

12. The process as recited in claim 1 wherein said alkyl is $C_1$-$C_4$ alkyl.

13. The process as recited in claim 1 wherein said heating is conducted for a period of time sufficient to racemize the optically active organic acid to an enantiomeric excess of less that about 50%.

14. The process as recited in claim 1 wherein said heating is conducted for a period of time sufficient to racemize the optically active organic acid to an enantiomeric excess of less that about 30%.

* * * * *

UNITED STATES PATENT AND TRADEMARK OFFICE
CERTIFICATE OF CORRECTION

PATENT NO. : 4,613,689
DATED : September 23, 1986
INVENTOR(S) : Patricia Siuta-Mangano, Samun K. Dahod It is certified that error appears in the above—identified patent and that said Letters Patent is hereby corrected as shown below:

Col. 3, line 34 - "of the acid" should be -- of the aqueous acid --.

Col. 3, line 66 - "heated at" should be -- was heated at --.

Col. 4, line 1 - "obtained" should be -- was obtained --.

Col. 5, line 44 - "What is Claimed is:" should be a heading.

Col. 6, line 21 - In Claim 6, change dependency from "5" to -- 4 --.

Signed and Sealed this

Thirtieth Day of December, 1986

Attest:

DONALD J. QUIGG

Attesting Officer

Commissioner of Patents and Trademarks